United States Patent [19]

Inoue et al.

[11] Patent Number: 5,670,328

[45] Date of Patent: Sep. 23, 1997

[54] MONOCLONAL ANTIBODIES TO HUMAN PULMONARY SURFACTANT APOPROTEIN D AND USE THEREOF

[75] Inventors: Takeshi Inoue, Katori-gun; Eiji Matsuura, Choshi; Yoshio Kuroki, Sapporo; Toyoaki Akino, Sapporo; Shosaku Abe, Sapporo, all of Japan

[73] Assignee: Yamasa Corporation, Chiba-ken, Japan

[21] Appl. No.: 400,530

[22] Filed: Mar. 7, 1995

Related U.S. Application Data

[63] Continuation of Ser. No. 190,193, Feb. 9, 1994, abandoned.

[30] Foreign Application Priority Data

Jun. 9, 1992 [JP] Japan ................................. 4-174786
Sep. 29, 1992 [JP] Japan ................................. 4-283961

[51] Int. Cl.$^6$ ............................................. G01N 33/53
[52] U.S. Cl. ..................... 435/7.23; 435/7.1; 435/40.52; 436/518; 436/536; 436/548; 436/907; 530/388.2; 530/388.25; 530/388.85; 530/391.3
[58] Field of Search .................... 435/7.23, 810, 435/975, 7.1, 40.52; 436/518, 536, 548, 907; 530/388.2, 388.25, 388.85, 391.3

[56] References Cited

U.S. PATENT DOCUMENTS 4,562,003 12/1985 Lewicki ........................... 260/112 B
5,156,950 10/1992 Akino .............................. 435/7.51

FOREIGN PATENT DOCUMENTS 0 203 093B1 12/1986 European Pat. Off. .
61-277699 12/1986 Japan .
62-64956 3/1987 Japan .
4-9665 1/1992 Japan .
89-01624 2/1989 WIPO .
89-02075 3/1989 WIPO .

OTHER PUBLICATIONS

Shimizu et al., "Primary Structure of Rat Pulmonary Surfactant Protein D", Journal of Biological Chemistry, vol. 267, No. 3, Jan. 25, 1992, pp. 1853–1857.

Persson et al., "Surfactant Protein D is a Divalent Cation-–Dependent Carbohydrate–Binding Protein", vol. 265, No. 10, Apr. 5, 1990, pp. 5755–5760.

Archives of Biochemistry and Biophysics, "Human Surfactant Protein D: SP–D Contains a C–Type Lectin Carbohydrate Recognition Domain", Rust et al., vol. 290, No. 1, Oct., pp. 116–126 (1991).

*Primary Examiner*—Carol A. Spiegel
*Attorney, Agent, or Firm*—Wenderoth, Lind & Ponack

[57] ABSTRACT

A monoclonal antibody which is capable of specifically binding with human pulmonary surfactant apoprotein D has been successfully obtained. Using the monoclonal antibody, human pulmonary surfactant apoprotein D can be specifically detected and assayed, whereby diagnosis of respiratory diseases is enabled.

6 Claims, 13 Drawing Sheets

F I G. 12
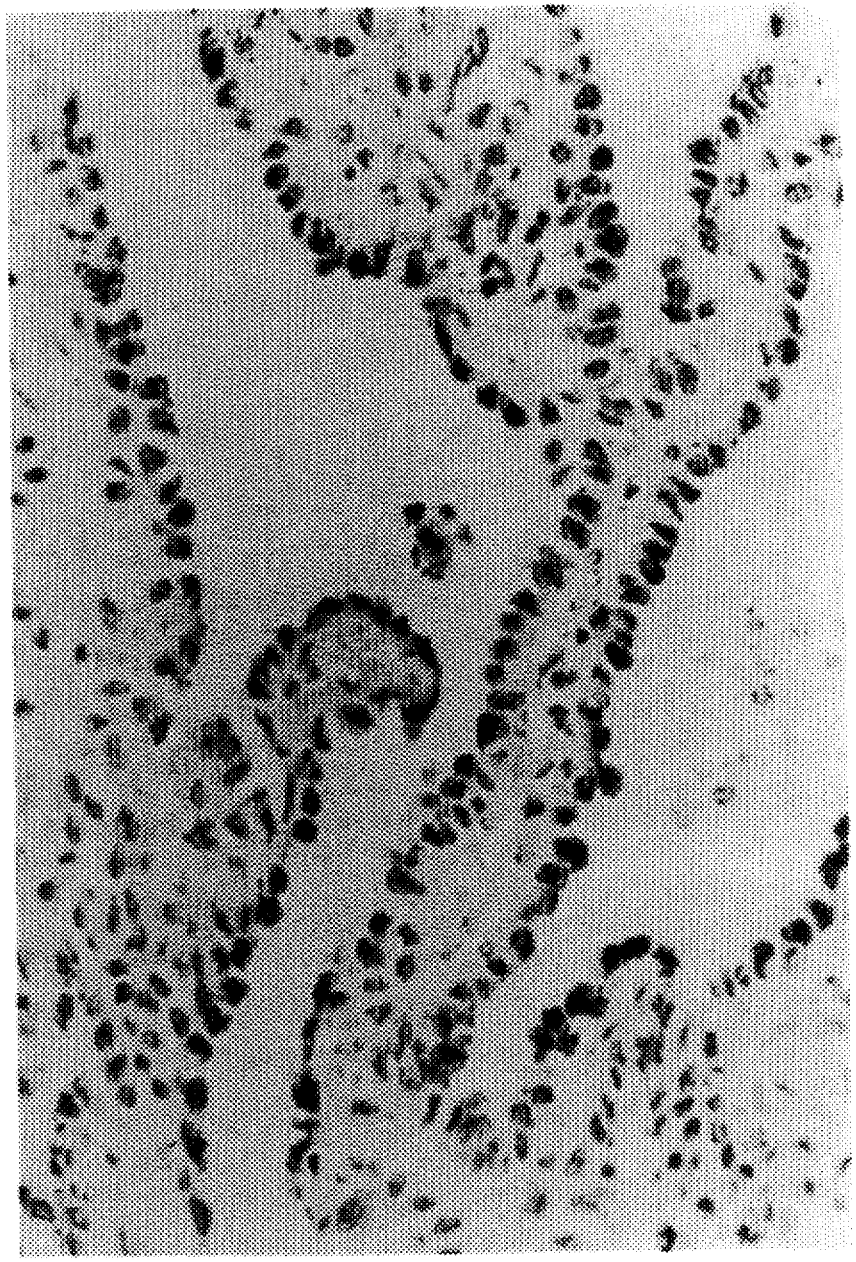

F I G. 13
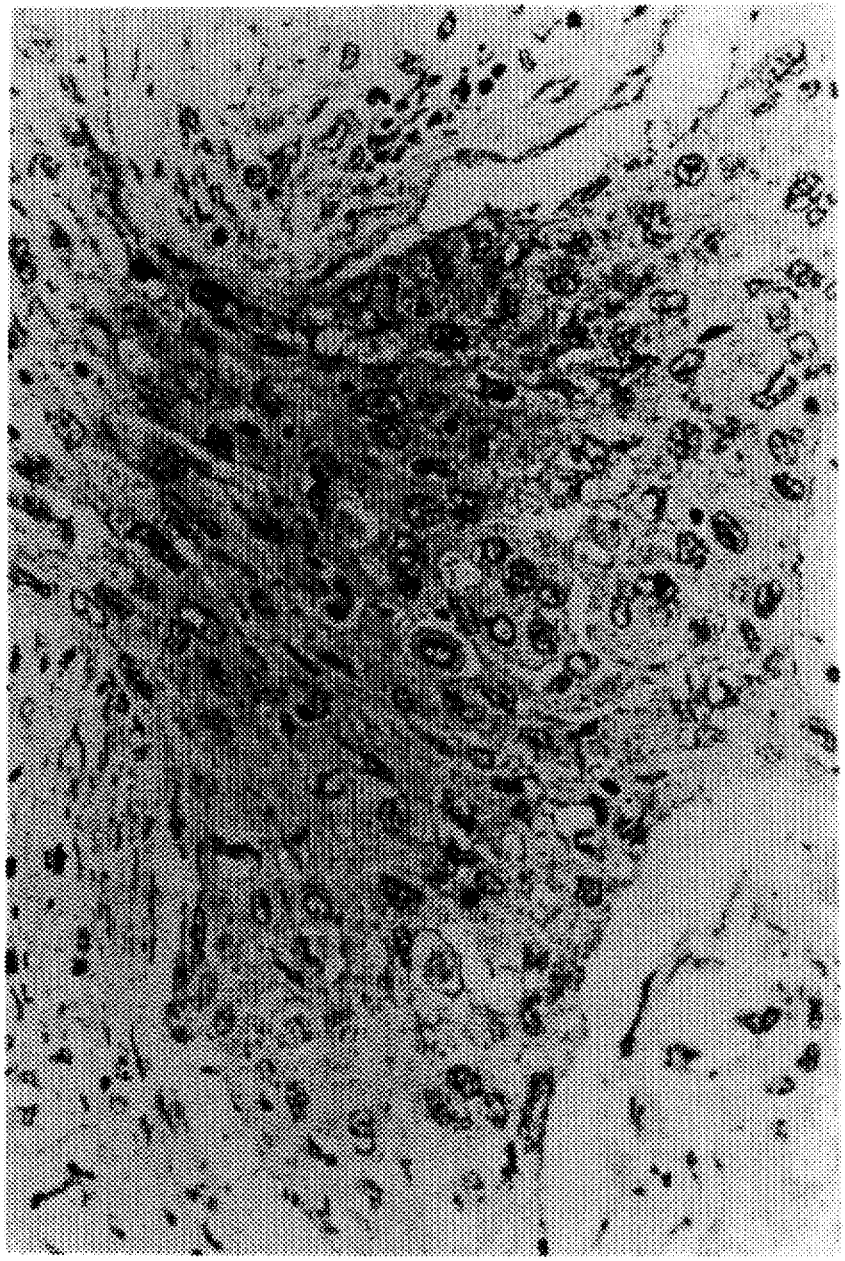

MONOCLONAL ANTIBODIES TO HUMAN PULMONARY SURFACTANT APOPROTEIN D AND USE THEREOF

This application is a continuation of now abandoned application Ser. No. 08/190,193, filed Feb. 9, 1994.

TECHNICAL FIELD

The present invention relates to a monoclonal antibody capable of specifically binding with human pulmonary surfactant apoprotein D and also relates to use thereof.

BACKGROUND ART

The lung is a vascular cavity organ and has the alveoli. The surfaces of the alveoli which take the inhaled air directly are covered with the mantle called the alveolar lining layer. The major components of the alveolar lining layer consist of pulmonary surfactant abundant in phospholipids.

The pulmonary surfactant is a lipoprotein composed of about 10% proteins and phospholipids, the components of which are mainly dipalmitoylphosphatidyl choline and phosphatidyl glycerol (abbreviated as DPPC and PG, respectively). The pulmonary surfactant exerts the function in such a way that it reduces the surface tension of the alveoli wherein phospholipids are aligned on the surface at the air-fluid boundary. Therefore, for example, the amount of the pulmonary surfactant in the amniotic fluid is considered to reflect maturity of the lung of the fetus.

The protein moiety in the pulmonary surfactant is called pulmonary surfactant apoprotein, and there have been hitherto known four (4) proteins of pulmonary surfactant apoprotein family, i.e., A, B, C and D. Recent studies have been clarifying that the protein moiety plays an important role in exhibiting the function of pulmonary surfactant, regulation of metabolism, defense mechanism in the body, and the like.

As diseases in association with the pulmonary surfactant, infant respiratory distress syndrome (IRDS), adult respiratory distress syndrome (ARDS) and the like have been reported. In the newborn infant with IRDS, the pulmonary surfactant content in the alveoli decreases so that the alveoli collapse. In such a case, the respiratory function cannot be maintained to be stable.

Thus, by determining the pulmonary surfactant content in the amniotic fluid prior to delivery, it may be predicted whether the coming baby might suffer from IRDS. When the fetus is suspected to suffer from IRDS, immediately after birth, the newborn infant can be medicated by liposome preparations of the surfactant.

In order to determine the pulmonary surfactant content in the amniotic fluid, conventional methods have been proposed wherein the proportion of lecithin to sphingomyelin (L/S ratio) or the amount of DPPC has been determined in consideration for phospholipids. However, these methods encounter various problems and are still unsatisfactory, due to low correlation to disease, lack of quantitative determination, or difficulties in operability.

To solve the problems in the prior arts which have conventionally focused on phospholipids, it has been attempted to detect or determine pulmonary surfactant by taking notice of the protein moiety of pulmonary surfactant, i.e., pulmonary surfactant apoprotein, and using antibodies to the protein (cf., e.g., Japanese Patent KOKAI (Laid-Open) Nos. 62-64956 and 4-9665, WO 89/02075, WO 89/01624).

As stated above, it is known that 4 kinds of proteins A through D exist in human pulmonary surfactant apoprotein. Human pulmonary surfactant apoprotein A is a hydrophilic protein having a molecular weight of 28 to 38 kDa under a reduced condition, and participates predominantly in regulation of pulmonary surfactant metabolism. Human pulmonary surfactant apoproteins B and C are hydrophobic proteins having molecular weights of 8 kDa under a reduced condition and 3 to 4 kDa under a reduced, condition, respectively. Both surfactant proteins B and C play a role mainly in exhibiting the function of pulmonary surfactant.

Human pulmonary surfactant apoprotein D is a hydrophilic protein having a molecular weight of 43 kDa under a reduced condition. While the function has not been fully clarified, it has been reported that pulmonary surfactant apoprotein D would have the action different from those of pulmonary surfactant apoprotein A, B and C. Furthermore, the change with time passage in pulmonary surfactant apoprotein D content in the amniotic fluids is also different from that of pulmonary surfactant apoprotein A. In association with the function, research interests have been directed to detection of pulmonary surfactant apoprotein D in the lung tissues, and also directed to quantitative determination of pulmonary surfactant apoprotein D in blood, bronchoalveolar lavage fluids and amniotic fluids, and accurate determination of change with time passage in the pulmonary surfactant apoprotein D content.

Therefore, an object of the present invention is to provide a monoclonal antibody which makes it possible to specifically detect or determine human pulmonary surfactant apoprotein D.

Another object of the present invention is to provide a method for specifically detecting or determining human pulmonary surfactant apoprotein D and a kit for use in the method, utilizing the monoclonal antibody thus provided.

DISCLOSURE OF THE INVENTION

In order to achieve the foregoing objects, the inventors have made extensive studies and succeeded in efficiently obtaining a monoclonal antibody for achieving the above objects. Based on the finding that human pulmonary surfactant apoprotein D can be specifically detected or determined using the monoclonal antibody, the present invention has thus been accomplished.

Therefore, as a first aspect, the present invention is directed to a monoclonal antibody capable of specifically binding with human pulmonary surfactant apoprotein D.

As a second aspect, the present invention is directed to a method for determination of human pulmonary surfactant apoprotein D using the monoclonal antibodies as reagents for the determination, and also directed to a kit for use in the method.

As a third aspect, the present invention is directed to a method for detecting the presence of human pulmonary surfactant apoprotein D in human lung tissues and a kit for use in the method, using the monoclonal antibody as an antibody reagent.

BRIEF DESCRIPTION OF THE DRAWINGS

FIG. 12 shows the results obtained by immunologically staining adenocarcinoma using the monoclonal antibody, 6B2.

FIG. 13 shows the results obtained by immunologically staining squamous cell carcinoma tissue using the monoclonal antibody, 6B2.

BEST MODE FOR CARRYING OUT THE INVENTION

Figure 1:
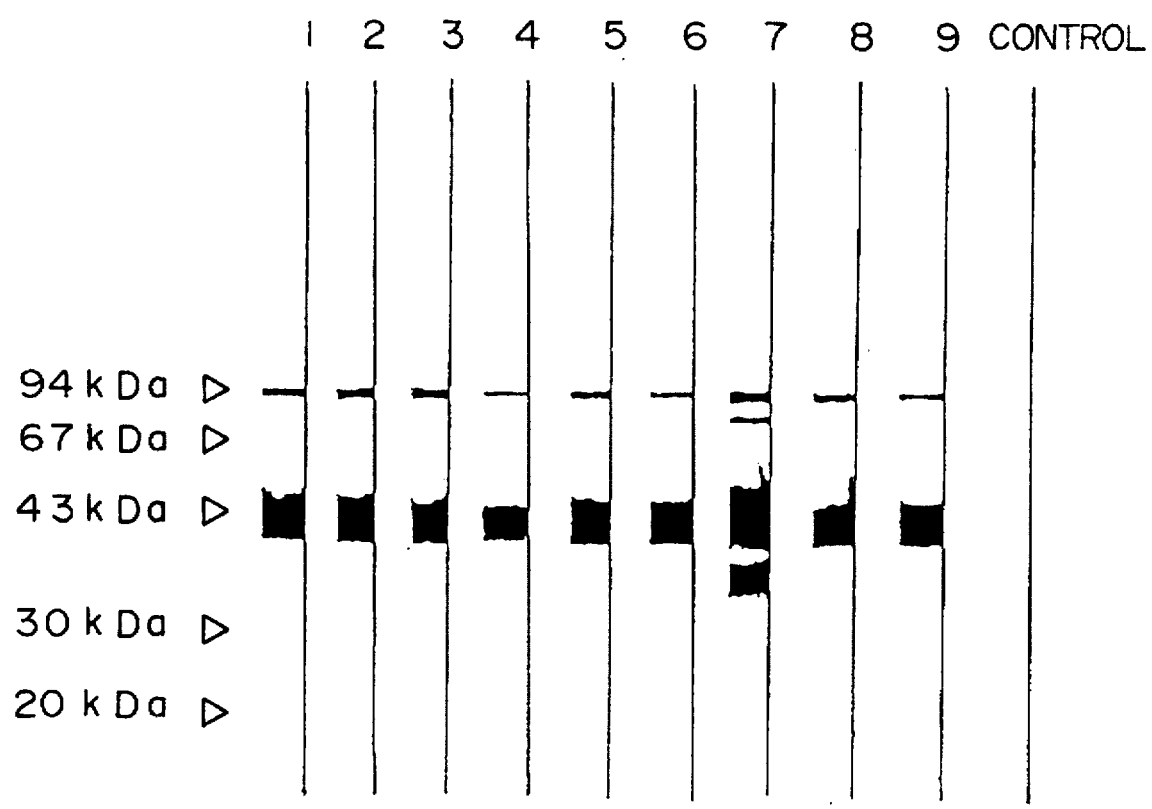
FIG. 1 shows specificity of the monoclonal antibody in immunoblotting.

The present invention is described below in more detail.

1. Monoclonal antibodies (1) Properties

The monoclonal antibody of the present invention is capable of specifically binding with human pulmonary surfactant apoprotein D. The monoclonal antibody is not limited by any other properties, but typically has the properties as set forth hereinbelow. The use of such a monoclonal antibody has enabled for the first time to specifically detect or determine human pulmonary surfactant apoprotein D in a sample solution.

(1)-1. Specificity

As shown in Examples herein, studies on the specificity of the antibodies by immunoblotting reveal that the monoclonal antibody reacts specifically with human pulmonary surfactant apoprotein D.

(1)-2. Reactivity

As shown in Examples herein, studies on the reactivity of the antibodies by ELISA reveal that the monoclonal antibody reacts with human pulmonary surfactant apoprotein D dependently on the concentration of the antibody.

(1)-3. Cross-reactivity

As shown in Examples herein, studies on the reactivity of the monoclonal antibody by immunoblotting and sandwich ELISA reveal that the monoclonal antibody does not substantially react with human-derived pulmonary surfactant apoproteins A, B and C, or even if it reacts with these apoproteins, there is no adverse influence on measurement of human pulmonary surfactant apoprotein D.

(1)-4. Species specificity

As shown in Examples herein, studies on the reactivity of the monoclonal antibody by immunoblotting and sandwich ELISA reveal that the monoclonal antibody does not substantially react with pulmonary surfactant apoprotein D derived from other animal including rat, or even if it reacts with these apoproteins, there is no adverse influence on measurement of human pulmonary surfactant apoprotein D.

(2) Production

The monoclonal antibody of the present invention as described hereinabove can be produced in a conventional manner. As an immunogen, human pulmonary surfactant apoprotein D is used. The human pulmonary surfactant apoprotein D can be prepared from, e.g., the bronchoalveolar lavage fluids, preferably from the bronchoalveolar lavage fluids of patients with pulmonary alveolar proteinosis, according to the method of Persson et al., J. Biol. Chem., 265, 5755, 1990 and the like. There is no particular limitation to the purity degree of the immunogen.

Alternatively, a peptide corresponding partially to the amino acid sequence of human pulmonary surfactant apoprotein D is chemically synthesized with a conventional manner and the thus synthesized peptide may also be used as the immunogen. Where the peptide synthesized has merely a low antigenicity, the conjugate with a high molecular carrier may be preferably used as the immunogen. Such a carrier is conventionally used for preparing a hapten antigen, and includes bovine serum albumin, Keyhole limpet hemocyanin and the like. Furthermore, recombinant human pulmonary surfactant apoprotein D prepared with a recombinant DNA technology may also be used as an immunogen.

An animal to which the immunogen is administered may be any one of bovine, horse, sheep, goat, rat, mouse, guinea pig, dog, swine, rabbit, monkey, pigeon, chicken, and the like. Particularly, mouse, rat, guinea pig, rabbit and goat are preferred.

The immunogen is administered to such an animal in a conventional manner. For example, an emulsion is prepared by mixing the immunogen with various adjuvants such as complete Freund's adjuvant, incomplete Freund's adjuvant, alum adjuvant, aluminum hydroxide adjuvant and pertussis adjuvant. The emulsion is administered to the animal intravenously, intraperitoneally, subcutaneously or intracutaneously.

A preferred dose is in the range of from 0.01 to 10 mg protein/animal in the case of using rabbit and guinea pig, and in the case of mouse and rat, in the range of from 0.001 to 1 mg protein/animal.

After the first administration, the animal is further boostered in the same dose as above approximately 1 to 5 times at the interval of 1 to 4 weeks to induce production of an antibody to human pulmonary surfactant apoprotein D. Then, antibody-producing cells such as spleen cells, lymph node cells and peripheral blood lymphocytes are collected from the antibody production-induced animal in a conventional manner.

As myeloma cells used to fuse with the antibody-producing cells, there may be used established cells derived from various animals such as mouse, rat and human which are readily accessible. Preferred cell lines used are those having such properties that they have a chemical resistance, cannot survive in a selective medium in a non-fused state but can survive only in the state fused with the antibody-producing cells. In general, 8-azaguanine-resistant cells are used. This cell line is deficient of hypoxanthine guanine phosphoribosyl transferase and cannot thus grow in hypoxanthine-aminopterin-thymidine (HAT) medium. In terms of the cell properties, a cell line which does not secrete immunoglobulin, so-called a non-secretory cell line is preferred.

Specific examples of myeloma cell line include myeloma cell line such as P3x63Ag8 (ATCC TIB-9) (Nature, 256, 495–497 (1975)), P3x63Ag8U.1 (P3U1) (ATCC CRL-1597) (Current Topics in Microbiology and Immunology, 81, 1–7 (1978)), P3x63Ag8.653 (ATCC CRL-1580) (J. Immunology, 123, 1548–1550 (1979)), P2/NSI/1-Ag4-1 (ATCC TIB-18) (European J. Immunology, 6, 511–519 (1976)) and Sp2/0-Ag14 (ATCC CRL-1581) (Nature, 276, 269–270 (1978)); rat myeloma cell line such as 210.RCY.Ag1.2.3 (Y3-Ag1. 2. 3) (ATCC CRL-1631)

(Nature, 277, 131–133 (1979)); human myeloma cell line such as U-266-AR1 (Proc. Natl. Acad. Sci. U.S.A., 77, 5429 (1980)), GM1500 (Nature, 288, 488 (1980)) and KR-4 (Proc. Natl. Acad. Sci. U.S.A., 79, 6651 (1982)).

For cell fusion, myeloma cells compatible with the antibody-producing cells are chosen.

The cell fusion is carried out efficiently in a conventional manner, e.g., by mixing $10^6$ to $10^8$ cells/ml of myeloma cells with the antibody-producing cells in a mixing ratio of 1:4 to 10 and contacting the cells with each other for 1 to 10 minutes at 37° C. in animal cell culture medium such as Eagle's minimum essential medium (MEM), Dulbecco's modified Eagle's medium (DMEM) and RPMI-1640 medium. To accelerate the cell fusion, it is advantageous to use a cell fusion accelerator such as polyethylene glycol (PEG) having an average molecular weight of 1,000 to 6,000, polyvinyl alcohol and Sendai virus. The cell fusion between the antibody-producing cells and myeloma cells may also be accelerated by means of a commercially available cell fusion device utilizing an electric pulse.

In order to select a desired hybridoma from the cells after the cell fusion treatment, selective proliferation of the cells in a selective medium can be used. The selection is made, for example, by diluting the cell suspension with 15% fetal calf serum (FCS)-containing RPMI-1640 medium and the like to an appropriate dilution degree, inoculating the diluted suspension on a microplate in approximately $10^3$ to $10^6$ cells/well, adding a selective medium (e.g., HAT medium) to each well and then further culturing by suitably exchanging the selective medium with another. Where a 8-azaguanine-resistant strain is used as the myeloma cell and HAT is used as the selective medium, myeloma cells not fused are dead within ten (10) days from the start of culture and the antibody-producing cells which are normal cells cannot grow in vitro over long periods of time. Thus, the cells which grow after 10 to 14 days can be acquired as the desired hybridoma cells.

The hybridoma capable of producing the monoclonal antibody which recognizes human pulmonary surfactant apoprotein D can be surveyed by enzyme immunoassay (EIA, ELISA), radioimmunoassay (RIA) and the like. The survey can be made by, e.g., adding the culture supernatants containing the monoclonal antibodies to 96 well microplates for ELISA, to which human pulmonary surfactant apoprotein D has been previously adsorbed, to react the monoclonal antibodies with human pulmonary surfactant apoprotein D, then reacting the bound specific antibodies either with enzyme-labeled anti-immunoglobulin antibody or with biotin-labeled anti-immunoglobulin antibody and then with enzyme-conjugated avidin D, and in any case, then adding an enzyme substrate to each well to form a color. By selecting the culture supernatant which forms a color only in the human pulmonary surfactant apoprotein D-adsorbed well, the desired hybridoma capable of producing the desired antibody which specifically reacts with human pulmonary surfactant apoprotein D can be detected.

In the screening as described above, it is preferred to use highly purified human pulmonary surfactant apoprotein D. The monoclonal antibody of the present invention can be efficiently screened by using human pulmonary surfactant apoprotein D having a purity of 90% or more.

Cloning of the hybridoma can be performed by limiting dilution method, soft agar method, fibrin gel method, fluorescence-excited cell sorter method and the like.

The monoclonal antibody can be produced from the thus obtained hybridoma in a conventional manner such as cell culture and ascites formation.

According to cell culture, the hybridoma is cultured in a culture medium for animal cells, such as 10 to 15% FCS-containing RPMI-1640 medium and serum-free medium in a conventional manner, and the monoclonal antibodies can be collected from the culture supernatant.

In the method for recovering from the ascites, mineral oil such as pristane (2,6,10,14-tetramethyl-pentadecane) is intraperitoneally administered to animal histocompatible with the hybridoma, and the hybridoma is then intraperitoneally administered to the animal, e.g., in about $10^6$ cells/animal in the case of mouse. The hybridoma forms ascites tumor in about 10 to 18 days and the antibodies are produced in a high level in serum and the ascites.

Where it is required to purify the antibodies, the monoclonal antibody may be purified by appropriately choosing and combining therewith known methods such as ammonium sulfate salting; ion exchange chromatography utilizing anionic exchangers such as DEAE cellulose; affinity chromatography using protein A-SEPHAROSE (agarose gel); and molecular sieve chromatography.

2. Method for determination and a kit for use in the method

The method for determination of human pulmonary surfactant apoprotein D according to the present invention is characterized by using the monoclonal antibody as described above as a reagent. Principal, conditions and the like of the determination are not limited so long as the monoclonal antibody according to the invention are used as the reagent.

In terms of reaction mode for the determination, a competitive reaction and a non-competitive reaction (i.e., immunometric assay) are known. Any of those reactions may be applied to the present invention.

In terms of detection, there are known a non-labelling method (e.g., nephelometry) in which the result of antigen-antibody reaction is directly detected, and a labelling method in which the result may be detected using any marker. Any of those methods may be adopted in the present invention.

There are also known a heterogeneous method which requires BF separation and a homogeneous method which requires no BF separation. Any of those methods may be adopted in the present invention.

In terms of reaction phase, there are known a liquid phase method in which an overall reaction proceeds in the liquid phase and a solid phase method in which an immune reaction is carried out after the one partner of the immune reaction has been previously immobilized. Any of those methods may be adopted in the present invention.

The determination method of the present invention is performed by choosing from the various known techniques as described above the one suitable method depending on the purpose.

Details of these known techniques are described in the following publications which are incorporated herein by reference.

(1) "ZOKU RADIOIMMUNOASSAY (Radioimmunoassay, Sequel)" edited by Hiroshi Irie, published May 1, 1979 by KODANSHA Publishing Co.

(2) "KOSO MENEKI SOKUTEI-HO (Enzyme immunoassay)" edited by Eiji Ishikawa (second edition), published Dec. 15, 1982 by IGAKU SHOIN Publishing Co.

(3) "RINSHO BYORI (Clinical Pathology)", Extra Number, Special Issue "RINSHO KENSA NO TAMENO IMMUNOASSAY—GIJUTSU-TO-OYO (Immunoassay for Clinical Inspection—Technique and Application)", published in 1983 by RINSHO BYORI KANKOKAI (4) "BIOTECHNOLOGY JITEN (Dictionary of Biotechnology)", published Oct. 9, 1986 by CMC (5) Methods in ENZYMOLOGY Vol. 70 (Immunochemical techniques (Part A))

(6) Methods in ENZYMOLOGY Vol. 73 (Immunochemical techniques (Part B))

(7) Methods in ENZYMOLOGY Vol. 74 (Immunochemical techniques (Part C))

(8) Methods in ENZYMOLOGY Vol. 84 (Immunochemical techniques (Part D: Selected Immunoassay))

(9) Methods in ENZYMOLOGY Vol. 92 (Immunochemical techniques (Part E: Monoclonal Antibodies and General Immunoassay Methods))

(Articles (5)–(9) were published by Academic Press)

The monoclonal antibody of the present invention may be appropriately modified, if necessary and desired, into a form suitable for practical use in the selected method. Specific examples of such a form include a labelled antibody, an immobilized antibody and the like.

The monoclonal antibody may be used without any modifications, but in view of preventing non-specific adsorption, it is desired to use an active fragment of the monoclonal antibody.

The active fragment from the monoclonal antibody may take any form so long as the fragment maintains the characteristics of the monoclonal antibody. Such an active fragment includes $F(ab')_2$, Fab' and Fab. These active fragments can be prepared by a known process such as a restrictive digestion method wherein a purified antibody is digested with a protease such as papain, pepsin and trypsin (e.g., see "MENEKI SEIKAGAKU KENKYU-HO—ZOKU SEIKAGAKU JIKKEN KOZA 5 (Immunobiological Study—Sequel to Biochemical Experimental Lecture Series), edited by Japanese Biochemical Association, 89 (1986)).

As a marker bound to the antibody, there may be radioisotopes (e.g., $^{32}P$, $^{3}H$, $^{14}C$ and $^{125}I$), enzymes (e.g., β-galactosidase, peroxidase, alkaline phosphatase, glucose-6-phosphate dehydrogenase, catalase, glucose oxidase, lactate oxidase, alcohol oxidase and monoamine oxidase), coenzymes and prosthetic groups (e.g., FAD, FMN, ATP, biotin and hem), fluorescein derivatives (e.g., fluorescein isothiocyanate and fluorescein thioflubamyl), rhodamine derivatives (e.g., tetramethyl-rhodamine B isothiocyanate), fluorescent dyes (e.g., umbelliferone and 1-anilino-8-naphthalenesulfonic acid), and luminol derivatives (e.g., luminol, isoluminol and N-(6-aminohexyl)-N-ethylisoluminol). These markers are used to label the antibody or active fragment thereof, and the labelling is performed in a conventional manner suitably chosen from known techniques described in textbooks, e.g., "ZOKU SEIKAGAKU JIKKEN KOZA 5: MENEKI SEIKAGAKU KENKYU-HO (Sequel to Biochemical Experimental Lecture Series—Immunobiological Study), Tokyo Kagaku Dojin, 102–112, (1986)).

For immobilizing the antibody, a carrier is employed. Typical examples of the carrier include synthetic organic high molecular compounds such as polyvinyl chloride, polystyrene, styrene-divinylbenzene copolymer, styrene-maleic anhydride copolymer, nylon, polyvinyl alcohol, polyacrylamide, polyacrylonitrile, polypropylene and polymethylene methacrylate; polysaccharides such as agarose gel (e.g., SEPHAROSE and BIOGEL), cellulose (e.g., paper disc and filter paper); and inorganic high molecular substances such as glass, silica gel and silicone. These carriers may be introduced with functional groups such as an amino, aminoalkyl, carboxyl, acyl and hydroxy group, if desired. Substances with a low ability of binding to a protein are preferred as the carrier and in this regard, non-treated polystyrene and polyvinyl chloride are advantageously used.

The carrier may take any shape selected from plate-like (e.g., microtiter plate and disc), fibrous, membrane-like, fine particulate (e.g., latex particles), capsule-like, vesicular forms and the like. An appropriate shape of the carrier can be chosen depending upon assay mode to be practiced. Liposome (e.g., mono- or multi-layer lipid membrane) may also be used as a carrier for immobilizing the antibody.

The monoclonal antibody may be bound to the carrier by conventional methods, e.g., through physical adsorption, ionic bond, covalent bond, entrapping and the like (see, e.g., KOTEIKA KOSO (Immobilized Enzyme), edited by Ichiro Chihata, published Mar. 20, 1975 by Kodansha Publishing Co). Among them, physical adsorption is preferred because of the convenience. The binding between the monoclonal antibody and the carrier may be performed either directly or indirectly through other substances.

There is no particular restriction to a sample solution to be analyzed so long as the sample solution is suspected to contain human pulmonary surfactant apoprotein D therein. Typical examples of such a sample solution include amniotic fluids, bronchoalveolar lavage fluids, blood, serum and plasma.

The kit for use in the above assay method is characterized in that the monoclonal antibody of the present invention is contained as one of constituent reagents for the kit. Other reagents for the kit may be appropriately chosen depending upon assay method adopted.

Where a competitive reaction is adopted, the kit comprises, for example:

(1) an immobilized antigen or antibody, (2) a solution of a labeled antibody or antigen and, (3) a solution of an antigen having a known concentration.

Where a sandwich method is adopted, the kit comprises, for example:

(1) an immobilized first antibody, (2) a solution of a second antibody, (3) a solution of a labeled anti-immunoglobulin antibody and, (4) a solution of an antigen having a known concentration.

In the kits as described above, the terms "antibody" and "antigen" are, of course, used to mean the monoclonal antibody of the present invention and human pulmonary surfactant apoprotein D, respectively. As is recognized in the art, human pulmonary surfactant apoprotein D is a polyvalent antigen, and in the kit for use in the sandwich method, the "first antibody" and the "second antibody" may be those that recognize the same or different antigenic determinants on human pulmonary surfactant apoprotein D.

A modified kit for use in the assay based on the sandwich method comprises, for example:

(1) an immobilized first antibody, (2) a solution of a labeled second antibody and, (3) a solution of an antigen having a known concentration.

3. Method for detection and kit for use in the method

The characteristic feature for the method of the present invention resides in using as an antibody reagent the monoclonal antibody according to the present invention when detecting pulmonary surfactant apoprotein D in the lung tissue. Therefore, any markers, labelling of antibodies and methods for detection using labelled antibodies which are conventionally employed in immunological tissue diagnosis may also be applicable to the present invention.

That is, the radioisotopes, enzymes, coenzymes and prosthetic groups, fluorescent dyes, luminol derivatives and the like as described hereinabove can be used as markers. These markers may be bound either to the monoclonal antibody itself or to the fragment. The binding between the marker and the antibody or fragment thereof is effected in a conventional manner. The monoclonal antibody may also be indirectly labelled using a labelled anti-immunoglobulin antibody and the like.

The labeled antibody thus prepared is reacted with a lung tissue specimen in a conventional manner to visualize the marker bound to the antibody, wherein pulmonary surfactant apoprotein D in the lung tissue can be detected.

In case that enzyme is used as a marker in the assay method, the kit may comprise:

(1) an enzyme-labeled antibody and (2) a substrate solution.

When the biotin-avidin method is used, the kit comprises:

(1) a biotinylated antibody, (2) an enzyme-conjugated avidin and, (3) a substrate solution.

In the kit as described above, the term "antibody" means the monoclonal antibody of the present invention.

The present invention is described below in more detail by referring to examples.

EXAMPLE 1

Production of Mouse Monoclonal Antibody to Human Pulmonary Surfactant Apoprotein D (SP-D)

(1) Production of monoclonal antibody-producing hybridoma cells

Human SP-D prepared by known method (Persson, A. et al., J. Biol. Chem., 265, 5755 (1990)) was dissolved in physiological saline (0.4 mg/ml). The solution was mixed with complete Freund's adjuvant in 1:1 proportion. The resulting emulsion was intraperitoneally (i.p.) administered to BALB/c mouse (female, age of 6 weeks) in a dose of 20 μg/100 μl for initial immunization. After the initial immunization, the animal was boostered (i.p.) several times every other weeks in a similar manner. For the final booster, a physiological saline solution of human SP-D was intravenously (i.v.) administered to the animal at the tail vein in a dose of 5 μg/200 μl.

Three days after the final booster, mouse spleen was withdrawn and washed with RPMI-1640 medium to prepare spleen cells suspension. At the same time, mouse myeloma cells P3x63Ag8U1 (P3U1) (ATCC CRL-1597) were washed with RPMI-1640 medium. After the spleen cells were mixed with P3U1 in 10:1, the mixture was centrifuged and the resulting pellets were gradually added with 1 ml of RPMI-1640 medium containing polyethylene glycol (PEG) 1000 to perform cell fusion. RPMI-1640 medium was further added to the system to make the volume 10 ml. The mixture was then centrifuged and the resulting pellets were suspended in RPMI-1640 medium containing 1% fetal calf serum (FCS) in a concentration of $3 \times 10^4$ cells/0.1 ml when counted as P3U1. The suspension was separately charged by 0.1 ml in each well of 96-well microtiter plates. One day after, 0.1 ml each of hypoxanthine-thymidine-aminopterin-containing RPMI-1640 medium (HAT medium) was further added to each well. Then the half volume of the medium was replenished with fresh HAT medium every 3 or 4 other days.

Fourteen (14) days after the fusion, hybridoma cells were screened. That is, human SP-D (10 μg/ml) was previously coated and 50 μl of the culture supernatant was supplemented to each well of 96-well microtiter plates blocked with PBS containing 25% BLOCK ACE (manufactured by Dainippon Pharmaceutical Co., Ltd.), followed by reacting them at room temperature for an hour. After washing three (3) times with 200 μl of PBS, 50 μl of biotinylated anti-mouse IgG (manufactured by Vector Laboratories Inc.) solution was added to the system followed by reacting at room temperature for further an hour. After the reaction, the system was washed three (3) times with PBS, 50 μl of peroxidase-conjugated avidin D (manufactured by Vector Laboratories Inc.) solution was added to react them at room temperature for 30 minutes, the system was likewise washed with PBS, and then 200 μl of substrate solution (containing 0.25 mg/ml of 4-aminoantipyrine, 0.25 mg/ml of phenol and 0.425M hydrogen peroxide) was added to react them at room temperature. By measuring absorbance at 550 nm, antibodies which specifically reacted with human SP-D were detected and specific antibody-producing hybridoma cells were selected as shown in Table 1.

TABLE 1

| Antigen | Number of Specific Antibody-Positive Wells | Number of Wells where Cells Grew | Number of Total Wells |
| --- | --- | --- | --- |
| Human SP-D | 94 | 660 | 940 |

The thus selected hybridoma cells were cloned by the limiting dilution method and nine (9) hybridoma cell lines were established (1G11, 3E4, 3H4, 5A4, 6B2, 7A10, 7C6, 9E1 and 10H11 ). These hybridoma cells produced antibodies to human SP-D which showed extremely high specificity.

(2) Production and purification of monoclonal antibodies

These nine (9) hybridoma cells established were intraperitoneally administered in $3 \times 10^6$, respectively, to mouse previously treated with 0.5 ml of pristane. About two (2) weeks after, the ascites was collected. Then the ascites was subjected to affinity chromatography on Protein A-SEPHAROSE CL4B column to purify IgG from the fluid. First, 20 ml of Protein A-SEPHAROSE CL4B (manufactured by Pharmacia Biotech AB) was packed in a glass column of 1.5×20 cm and then equilibrated with 1.5M glycine buffer solution (pH 8.9) containing 3M sodium chloride. Then, the ascites was diluted to 2-fold with the equal volume of the glycine buffer solution. The diluted ascites was passed through the column. After washing and removing non-adsorbed protein with a sufficient volume of the glycine buffer solution, the adsorbed IgG was eluted with 0.1M citrate buffer solution (pH 3.0). The thus obtained IgG fraction was immediately dialyzed against PBS overnight to avoid denaturation.

EXAMPLE 2

Analyses (1) of Monoclonal Antibodies on Properties (Survey of Class and Type)

After human SP-D (10 μg/ml) was coated, the culture supernatants of each hybridoma cell or each solution of the purified monoclonal antibodies was added to 96-well microtiter plates blocked with PBS containing 25% BLOCK ACE (manufactured by Dainippon Pharmaceutical Co., Ltd.). Class and type of the antibodies were identified using MonoAb-ID EIA Kit (manufactured by Zymed Laboratories Inc.). The results are shown in Table 2.

TABLE 2

| Clone | IgG Class/Type |
| --- | --- |
| 1G11 | IgG1/κ |
| 3E4 | IgG1/κ |
| 3H4 | IgG1/κ |
| 5A4 | IgG2a/κ |
| 6B2 | IgG1/κ |
| 7A10 | IgG1/κ |
| 7C6 | IgG1/κ |
| 9E1 | IgG1/κ |
| 10H11 | IgG1/κ |

EXAMPLE 3

Analyses (2) of Monoclonal Antibodies on Properties (Antigenic Specificity of Monoclonal Anti-human SP-D Antibody)

The antigenic specificity of the monoclonal antibodies produced by the hybridoma cells (i.e., 1G11, 3E4, 3H4, 5A4, 6B2, 7A10, 7C6, 9E1 and 10H11) were verified by immunoblotting using sodium dodecyl sulfate-polyacrylamide gel electrophoresis (SDS-PAGE) and by enzyme immunoassay (ELISA). The name of each monoclonal antibody is the same as the hybridoma producing the antibody.

(A) Analyses of specificity by immunoblotting

SDS-PAGE was performed by the method of Laemmli (Nature, 227, 680, 1972). The basic procedures of immunoblotting are as follows. That is, the separated gel obtained by SDS-PAGE was laid on nitrocellulose membrane. By applying 60V for 12 hours thereto, protein was transferred onto the nitrocellulose membrane. The thus obtained nitrocellulose membrane was cut into strips along the moving line of a sample solution. A part of the membrane strips was used to stain proteins with Amide Black. The other membrane strips were immersed at 37° C. for an hour in PBS containing 0.5% TRITON X-100 (surfactant) and 2% skimmed milk for blocking and reacted at room temperature for an hour with the monoclonal antibody solution appropriately diluted with PBS. After washing with PBS, the nitrocellulose membrane was reacted with peroxidase-labelled anti-mouse IgG antibody at room temperature for an hour. The nitrocellulose membrane was washed likewise and reacted with a substrate solution (containing 30 mg of COLOR DEVELOPER manufactured by Bio-Rad Laboratories Inc., 10 ml of methanol, 50 ml of PBS and 30 μl of 30% hydrogen peroxide). At the time when a color was appropriately formed, the system was washed with water to terminate the reaction.

Human SP-D shows a molecular weight of 43 kDa under a reduced condition. After the human SP-D fraction was electrophoresed under a reduced condition, the reaction specificity of each monoclonal antibody was examined by immunoblotting. As shown in FIG. 1, the nine (9) monoclonal antibodies (i.e., Lane 1: 1G11, Lane 2: 3E4, Lane 3: 3H4, Lane 4: 5A4, Lane 5: 6B2, Lane 6: 7A10, Lane 7: 7C6, Lane 8: 9E1 and Lane 9: 10H11 ) all showed extremely strong reactivity with human SP-D having a molecular weight of 43 kDa. Furthermore, the monoclonal antibody 7C6 showed extremely strong reactivity also with the degradation product of human SP-D having a molecular weight of about 38 kDa which was considered to be by-produced at the preparation process.

(B) Analyses of specificity by ELISA

Figure 2:
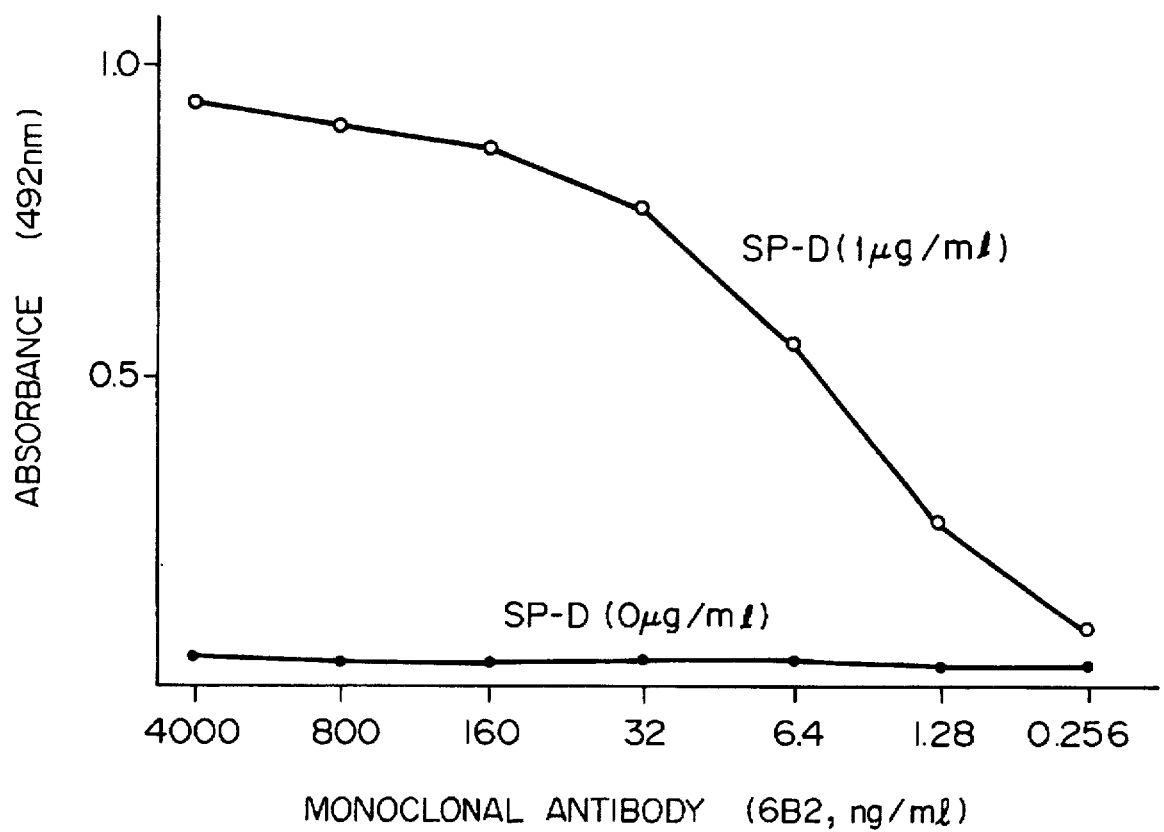
FIG. 2 shows reactivity of the monoclonal antibody, 6B2.
Figure 3:
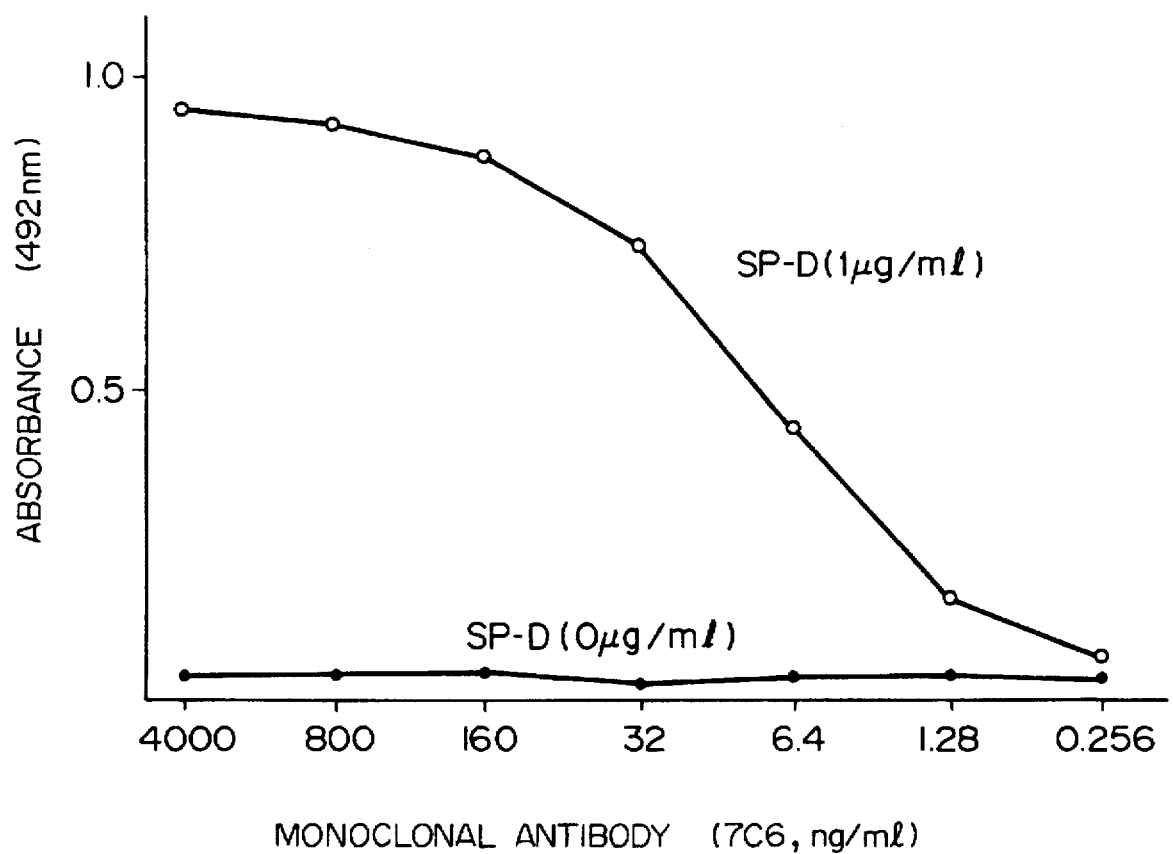
FIG. 3 shows reactivity of the monoclonal antibody, 7C6.

A solution of purified human SP-D in 5 mM Tris (1.0 μg/ml, pH 7.4) was added by 50 μl to each well of 96 well microtiter plates. After allowing to stand at 4° C. overnight, the plates were washed three (3) times with PBS. Each well was added with 200 μl of PBS containing 0.5% TRITON X-100 and 2% skimmed milk. The plates were allowed to react at room temperature for an hour to effect blocking. After washing three (3) times with PBS, 50 μl each of the monoclonal antibody solution was added to react at room temperature for an hour. After washing three (3) times with 200 μl of PBS, 50 μl of biotinylated anti-mouse IgG (manufactured by Vector Laboratories Inc.) solution was added to the system followed by reacting at room temperature for further an hour. After the reaction, the system was washed three (3) times with PBS and 50 μl of peroxidase-conjugated avidin D (manufactured by Vector Laboratories Inc.) solution was added to react them at room temperature for 30 minutes. The reaction mixture was likewise washed with PBS and 100 μl of substrate solution (0.1M citrate buffer solution, pH 5.9, containing 0.2 mg/ml of o-phenylenediamine and 0.425M hydrogen peroxide) was added to react them at room temperature. After adding 100 μl of 2 N sulfuric acid to terminate the reaction, the absorbance was measured at 492 nm. As shown in FIGS. 2 and 3, the reactivity of the monoclonal antibodies 6B2 and 7C6 with human SP-D (1.0 μg/ml) was dependent on the concentration of the antibodies. While the results are not shown, similar phenomena were confirmed with other monoclonal antibodies 1G11, 3E4, 3H4, 5A4, 7A10, 9E1 and 10H11.

EXAMPLE 4

Analyses (3) of Monoclonal Antibodies on Properties (Cross-reactivity of Monoclonal Anti-human SP-D Antibody)

The cross-reactivity of the monoclonal antibodies 6B2 and 7C6 produced by the hybridoma cells with human SP-A and rat SP-D was examined by immunoblotting using SDS-PAGE and sandwich ELISA.

Human and rat SP-D were prepared by the Persson et al. method supra and human SP-A was prepared by the method of Kuroki et al., Proc. Natl. Acad. Sci. U.S.A., 85, 5566, 1988.

(A) Analyses of cross-reactivity by immunoblotting

Human SP-D fraction, human SP-A fraction, rat SP-D fraction, and human amniotic fluids (38 weeks of pregnancy) were subjected to electrophoresis under a reduced condition and the cross-reactivity of the monoclonal antibodies was examined by immunoblotting.

Figure 4:
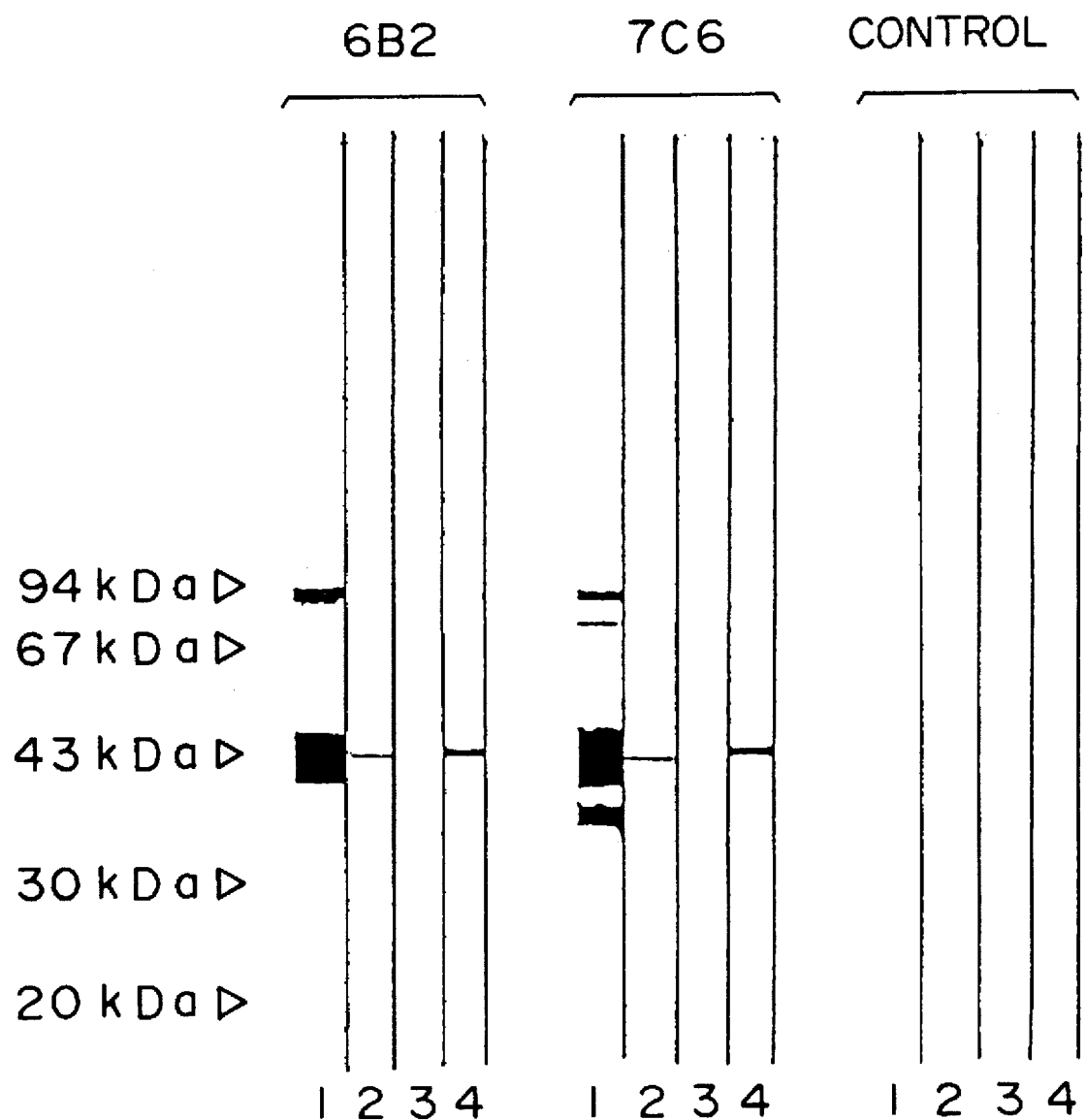
FIG. 4 shows cross-reactivity of the monoclonal antibodies, 6B2 and 7C6 in immunoblotting.

Based on the results of blotting (Lane 1: human SP-D, Lane 2: human SP-A, Lane 3: rat SP-D, Lane 4: human amniotic fluids), the respective monoclonal antibodies 6B2 and 7C6 showed extremely strong reactivity with human SP-D having a molecular weight of 43 kDa, protein of about 90 kDa which was considered to be a dimer of human SP-D, and SP-D in human amniotic fluids. Furthermore, the monoclonal antibody 7C6 showed extremely strong reactivity also with the degradation product of human SP-D having a molecular weight of about 38 kDa which was considered to be by-produced at the preparation process. On the other hand, the both monoclonal antibodies did not show any reactivity at all with human SP-A having a molecular weight of approximately 26 to 38 kDa under a reduced condition. The monoclonal antibodies only slightly reacted with human SP-D having a molecular weight of 43 kDa which was considered to be intermingled in the human SP-A fraction in a trace amount. The both monoclonal antibodies did not show significant reactivity with rat SP-D (having a molecular weight of about 43 kDa under a reduced condition, as shown in FIG. 4.

(B) Analyses of cross-reactivity by sandwich ELISA

The cross-reactivity of the monoclonal antibodies 6B2 and 7C6 of the invention to human SP-A and rat SP-D was examined by sandwich ELISA using the monoclonal antibodies. The basic procedures of sandwich ELISA are as follows.

A PBS solution (10 μg/ml) of each monoclonal antibody was added by 50 μl to each well of 96 well microtiter plates. After allowing to stand at 4° C. overnight, the plates were washed three (3) times with PBS. Each well was added with 200 μl of PBS containing 0.5% TRITON X-100 and 2% skimmed milk. The plates were allowed to stand for an hour at room temperature for blocking. After washing three (3) times with PBS, 50 μl of a solution of human SP-D in PBS was added to each well. The plates were allowed to stand at 4° C. overnight. After washing three (3) times with 200 μl of PBS, 50 μl of 10 μg/ml PBS solution (containing 0.5% TRITON X-100 and 0.1% skimmed milk) of biotinylated monoclonal antibody 7C6 was added to the system followed by reacting at room temperature for 4 hours. After the reaction, the system was washed three (3) times with PBS and 50 µl of peroxidase conjugated avidin D (manufactured by Vector Laboratories Inc.) solution was added to react them at room temperature for 30 minutes. The reaction mixture was likewise washed with PBS and 100 µl of substrate solution (0.2M citrate buffer solution, pH 3.8, containing 3 mM 3,3', 5,5'-tetramethylbenzidine and 0.005% hydrogen peroxide) was added to react them at room temperature. After adding 100 µl of 2N sulfuric acid to terminate the reaction, the absorbance was measured at 450 nm.

The cross-reactivity (%) was calculated according to the following equation.

$$\text{Cross-reactivity (\%)} = \frac{\text{human SP-D level for achieving 50\% binding property (corresponding to absorbance of 0.6) (50 ng/ml)}}{\text{level of analogous substance for achieving 50\% binding property (corresponding to absorbance of 0.6) (ng/ml)}} \times 100$$

Figure 5:
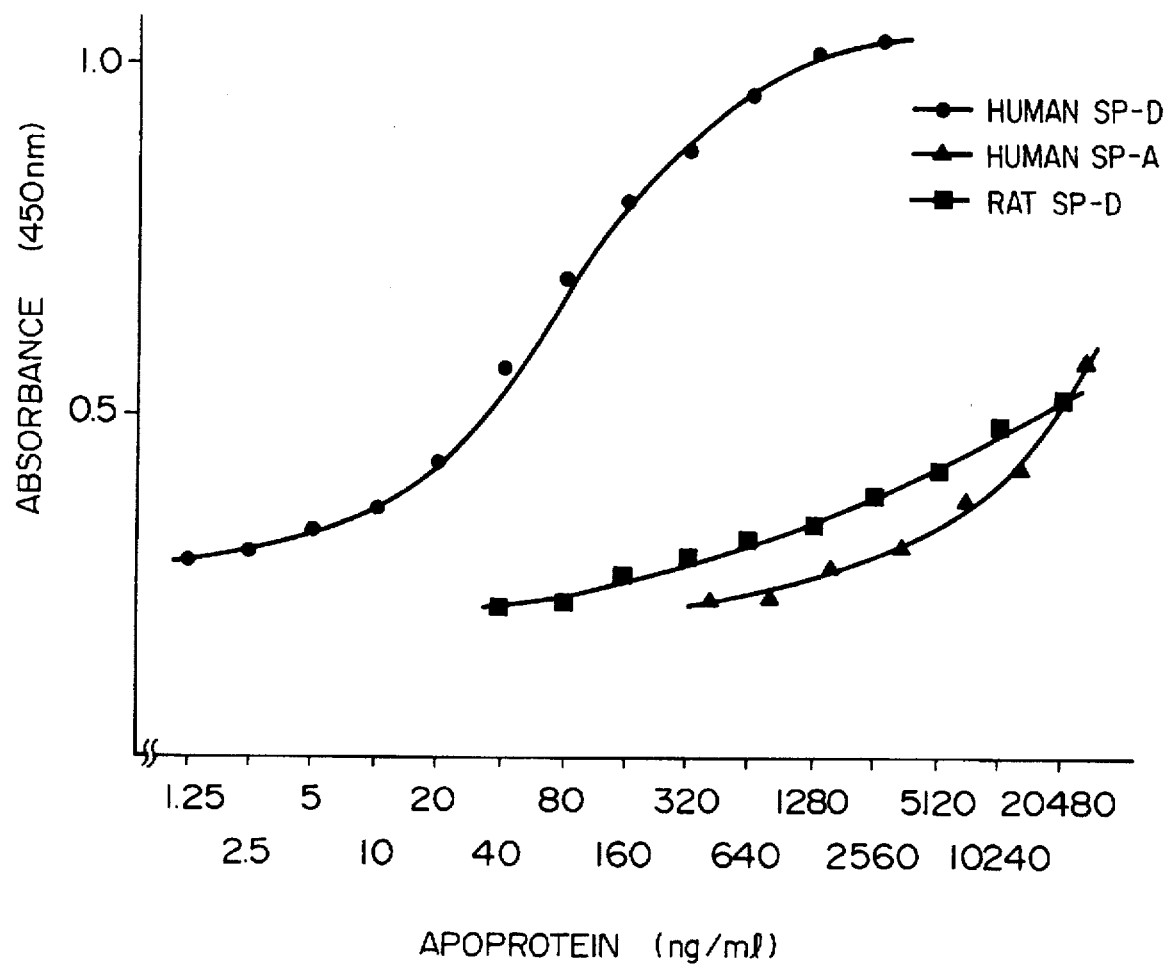
FIG. 5 shows cross-reactivity of the monoclonal antibodies, 6B2 and 7C6 7in the sandwich ELISA.

The results indicate that the cross-reactivity to human SP-A was less than 0.2% and that to rat SP-D was less than 0.25% as shown in FIG. 5 and Table 3.

According to analyses of the cross-reactivity by the aforesaid immunoblotting using the same samples, the monoclonal antibodies 6B2 and 7C6 did not show any cross-reactivity at all with human SP-A of 26 to 38 kDa, but reacted with SP-D which was considered to be present in the SP-A fraction in a trace amount. It is thus considered that the actual cross-reactivity to human SP-A would be much less.

TABLE 3

| Analogous Substance | Concentration for Achieving 50% binding (ng/ml) | Cross-reactivity (%) |
| --- | --- | --- |
| Human SP-D | 50 | 100 |
| Human SP-A | >25,000 | <0.2 |
| Rat SP-D | >20,000 | <0.25 |

(C) As stated above, the monoclonal antibodies of the present invention react specifically with human SP-D. By using immobilized monoclonal antibody 7C6 in combination with horseradish peroxidase-labelled monoclonal antibody 6B2 prepared by the method of Nakane et al., Immunoassays in the clinical laboratory, Alan R. Liss Inc., New York, 81, 1979, high sensitive sandwich ELISA specific for human SP-D was established. The basic procedure of sandwich ELISA are as follows.

A PBS solution (10 µg/ml) of the monoclonal antibody 7C6 was added by 100 µl to each well of 96 well microtiter plates. After allowing to stand at 4° C. overnight, the plates were washed three (3) times with PBS. Each well was added with 200 µl of PBS containing 1% bovine serum albumin (BSA). The plates were allowed to stand for an hour at room temperature for blocking. After washing three (3) times with PBS, each well was added with 100 µl of a solution of human SP-D in PBS containing 0.5% TRITON X-100. The plates were allowed to react at room temperature overnight. After washing three (3) times with 200 µl of PBS, 100 µl of 2 µg/ml PBS solution (containing 0.5% TRITON X-100 and 1% BSA) of horseradish peroxidase-labelled monoclonal antibody 6B2 was added to each well to react at room temperature for 2 hours. After the reaction, the plates were washed three (3) times with PBS and, 100 µl of a substrate solution (0.2M citrate buffer solution, pH 3.8, containing 0.3 mM 3,3', 5,5'-tetramethylbenzidine and 0.005% hydrogen peroxide) was added to react them at room temperature for 20 minutes. Then 100 µl of 2N sulfuric acid was added to terminate the reaction and, the absorbance was measured at 450 nm.

(1) Calibration curve

Figure 6:
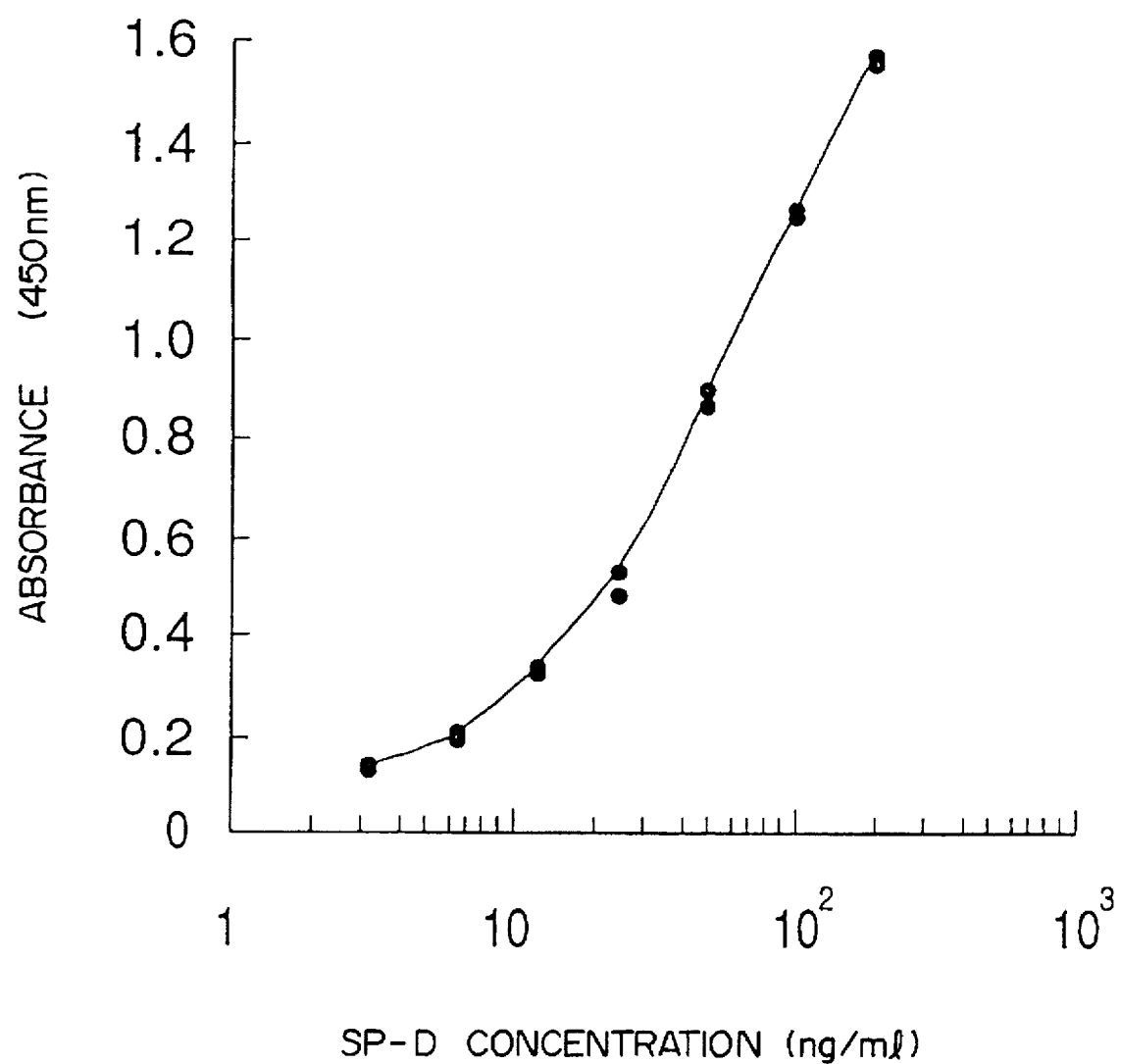
FIG. 6 shows a calibration curve in the sandwich ELISA.

Sandwich ELISA was performed using as a standard substance 0.5% TRITON X-100-containing PBS solution of purified human SP-D prepared by the method of Persson et al. supra. As the result, an excellent calibration curve dependent on concentration of human SP-D was obtained in the range of 3.13 ng/ml to 200 ng/ml, as shown in FIG. 6.

(2) Recovery test and dilution test

Figure 7:
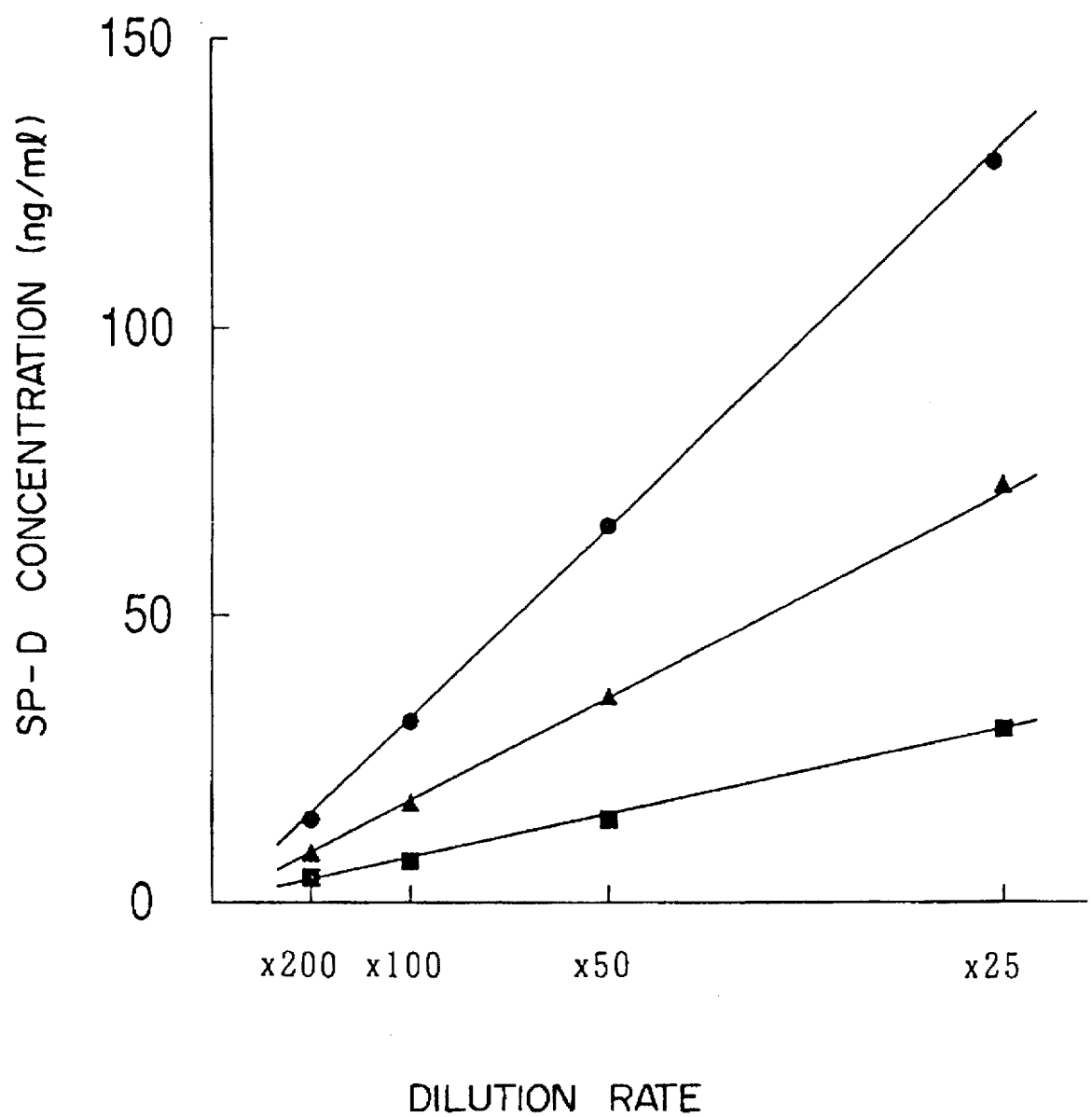
FIG. 7 shows the results of dilution test in the sandwich ELISA.

For the purpose of evaluating the basic efficiency of sandwich ELISA according to the present invention, a test of adding purified human SP-D to human amniotic fluids and recovering the added human SP-D from the fluids was carried out. A dilution test of human amniotic fluids was also carried out. In the recovery test, 0.5% TRITON X-100-containing PBS solution of purified human SP-D (0, 12.5, 25, 50 ng/ml) was added to human amniotic fluid samples and the human SP-D was assayed by sandwich ELISA. The results reveal that the purified human SP-D was recovered with a good recovery rate (i.e., 94.4 to 111.2%) as shown in Table 4. In the dilution test using human amniotic fluid samples, an excellent linear relationship was noted between the dilution magnification of the sample and the concentration of SP-D determined by ELISA, as shown in FIG. 7.

TABLE 4

| Sample | Amount of SP-D Added (ng/ml) | Data Observed (ng/ml) | Amount of SP-D Recovered (ng/ml) | Recovery Rate (%) |
| --- | --- | --- | --- | --- |
| 1 | 0 | 8.3 | | |
| | 12.5 | 20.4 | 12.1 | 96.8 |
| | 25.0 | 31.9 | 23.6 | 94.4 |
| | 50.0 | 56.0 | 47.7 | 95.4 |
| 2 | 0 | 14.0 | | |
| | 12.5 | 27.4 | 13.4 | 107.2 |
| | 25.0 | 38.4 | 24.4 | 97.6 |
| | 50.0 | 62.4 | 48.4 | 96.8 |
| 3 | 0 | 35.1 | | |
| | 12.5 | 49.0 | 13.9 | 111.2 |
| | 25.0 | 59.8 | 24.7 | 98.8 |
| | 50.0 | 82.4 | 47.3 | 94.6 |

(3) Cross-reactivity

In order to explore the cross-reactivity of sandwich ELISA to a substance analogous to human SP-D, serial dilutions of human SP-A, rat SP-D and human SP-D for control were prepared, and the reactivity was examined. The cross-reactivity was also calculated in accordance with the following equation.

$$\text{Cross-reactivity (\%)} = \frac{\text{human SP-D level for achieving 50\% binding property (60 ng/ml)}}{\text{level of analogous substance for achieving 50\% binding property (ng/ml)}} \times 100$$

The results indicate that the cross-reactivity to human SP-A was less than 0.3% and that to rat SP-D was 0.6%, as shown in Table 5.

According to analyses of the cross-reactivity by the aforesaid immunoblotting using the same samples, the monoclonal antibodies 6B2 and 7C6 did not show any cross-reactivity at all with human SP-A of 26 to 38 kDa but reacted with human SP-D which was considered to be present in the SP-A fraction in a trace amount. It is thus considered that the actual cross-reactivity to human SP-A would be much less.

TABLE 5

| Analogous Substance | Concentration for achieving 50% binding (ng/ml) | Cross-reactivity (%) |
|---|---|---|
| Human SP-D | 60 | 100 |
| Human SP-A | >20480 | <0.3 |
| Rat SP-D | 10240 | 0.6 |

EXAMPLE 5

Determination of SP-D Levels in Vital Samples

Following the sandwich ELISA in Example 4 (c), the SP-D levels were determined in the amniotic fluids from healthy normal pregnant women, in the bronchoalveolar lavage fluids obtained from the patients with pulmonary alveolar proteinosis, and in sera collected from the patients with interstitial pneumonia, pulmonary alveolar proteinosis and other respiratory diseases.

(A) SP-D levels in the amniotic fluids from healthy normal pregnant women

Figure 8:
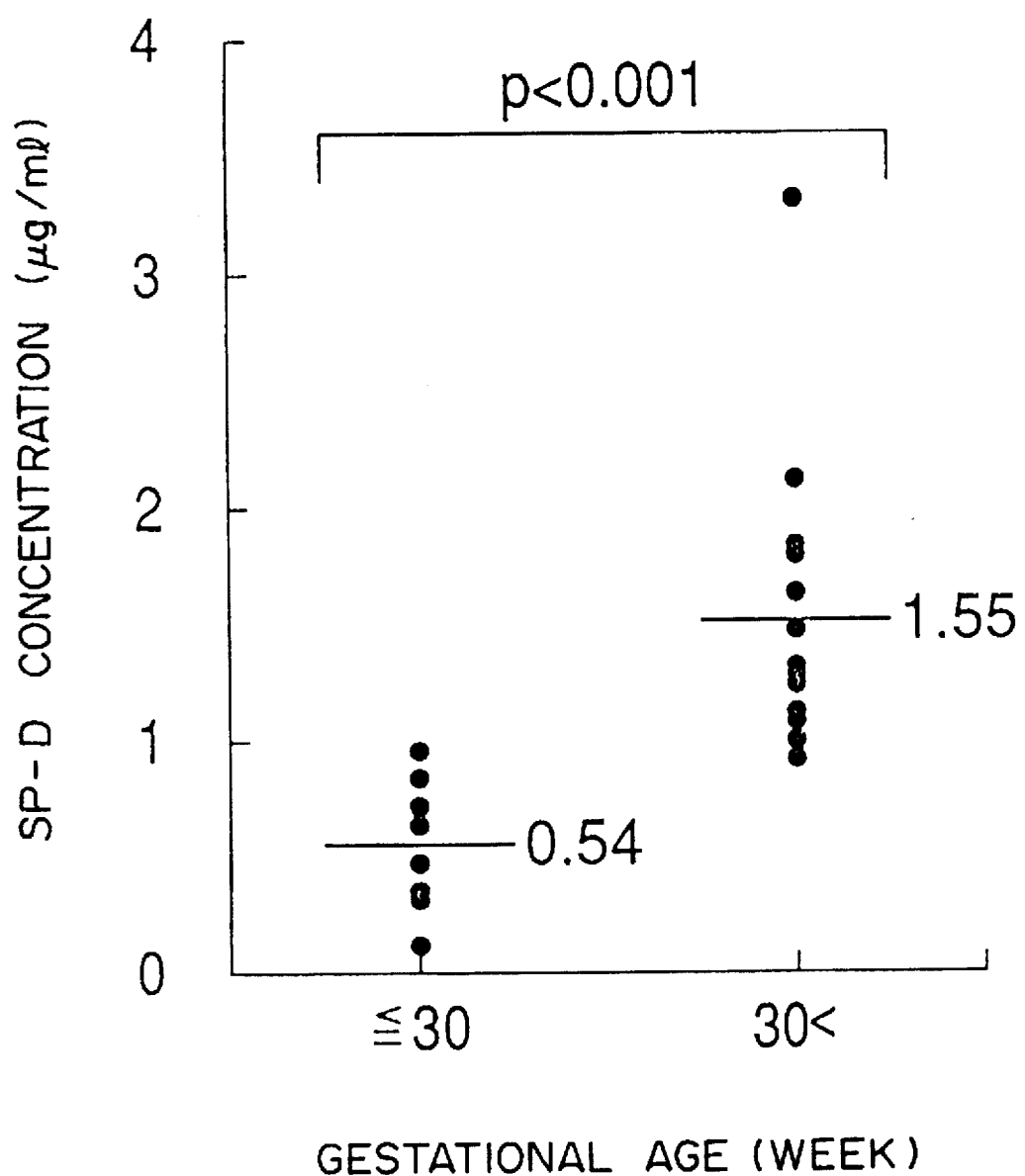
FIG. 8 shows the results of pulmonary surfactant apoprotein D (abbreviated as SP-D) levels in the amniotic fluids from pregnant women which have been determined by the sandwich ELISA.

The concentrations of SP-D in 21 amniotic fluid specimens obtained from healthy normal pregnant women of 26 to 40 weeks were determined. The results indicate that the SP-D concentrations in 13 amniotic fluids from mid-trimester pregnancies (over 30 weeks of gestation) were significantly higher than those of 8 amniotic fluids from late pregnancies (less than 30 weeks of gestation), as shown in FIG. 8. The results indicate that SP-D levels in amniotic fluids will reflect maturity of fetal lung and also suggest the possibility that determination of SP-D levels in amniotic fluids would be useful for diagnosis of IRDS in fetus.

(B) SP-D levels in bronchoalveolar lavage fluids

Figure 9:
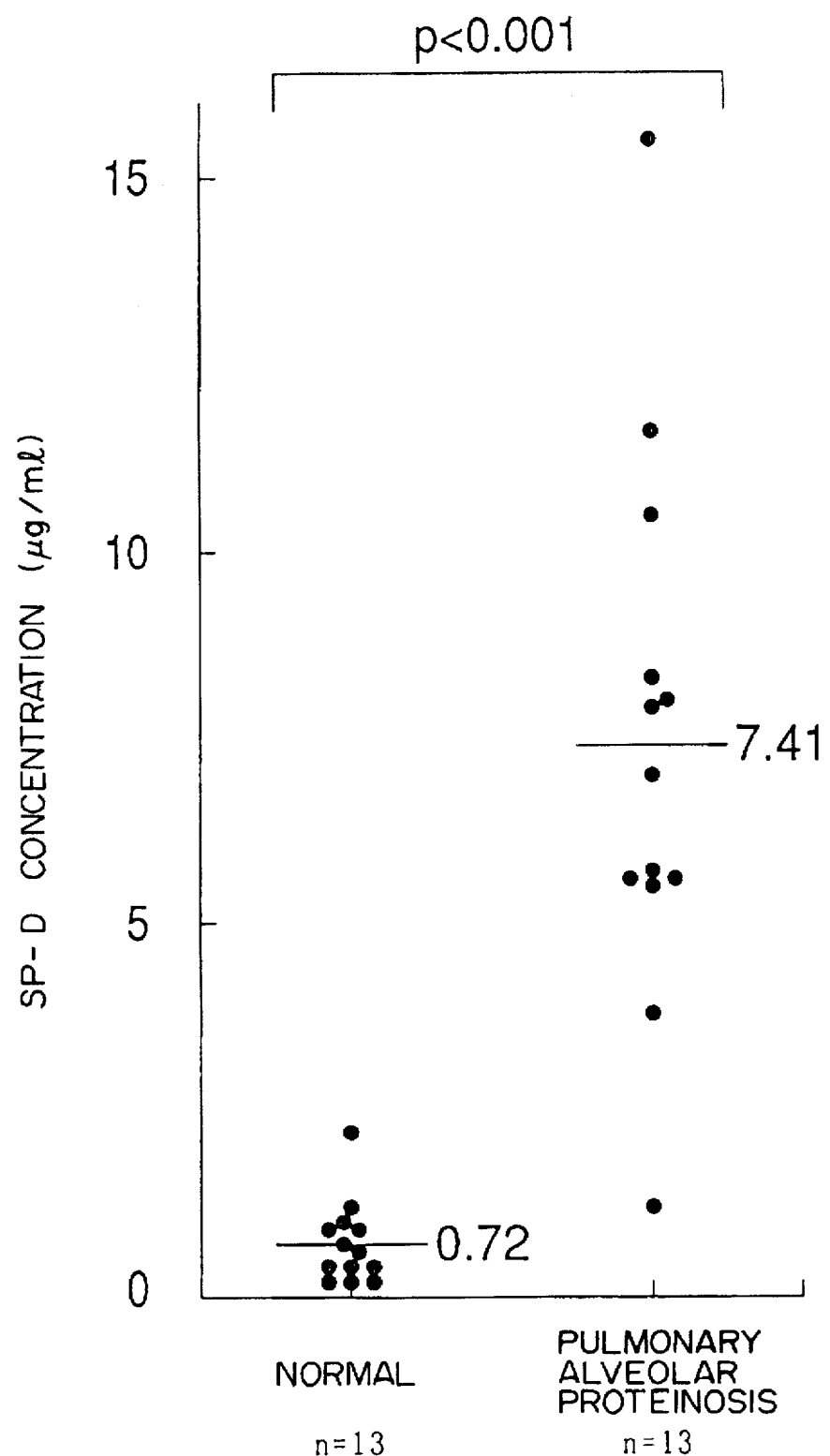
FIG. 9 shows the results of SP-D levels in bronchoalveolar lavage fluids from the patient with pulmonary alveolar proteinosis and from healthy volunteers which have been determined by the sandwich ELISA.

With respect to bronchoalveolar lavage fluids of the patients with pulmonary alveolar proteinosis (13 cases), idiopathic pulmonary fibrosis (IPF), and sarcoidosis (Sar), or that of healthy volunteers (13 cases), the SP-D levels were assayed. The results indicate that the SP-D levels were obviously higher in the patients with pulmonary alveolar proteinosis as compared to the healthy volunteers, as shown in FIG. 9. This suggests that determination of the SP-D levels in bronchoalveolar lavage fluids would be effective for diagnosis of patient with pulmonary alveolar proteinosis. In the patients with IPF and Sar, the SP-D levels were almost the same as that of the healthy volunteers.

Figure 10:
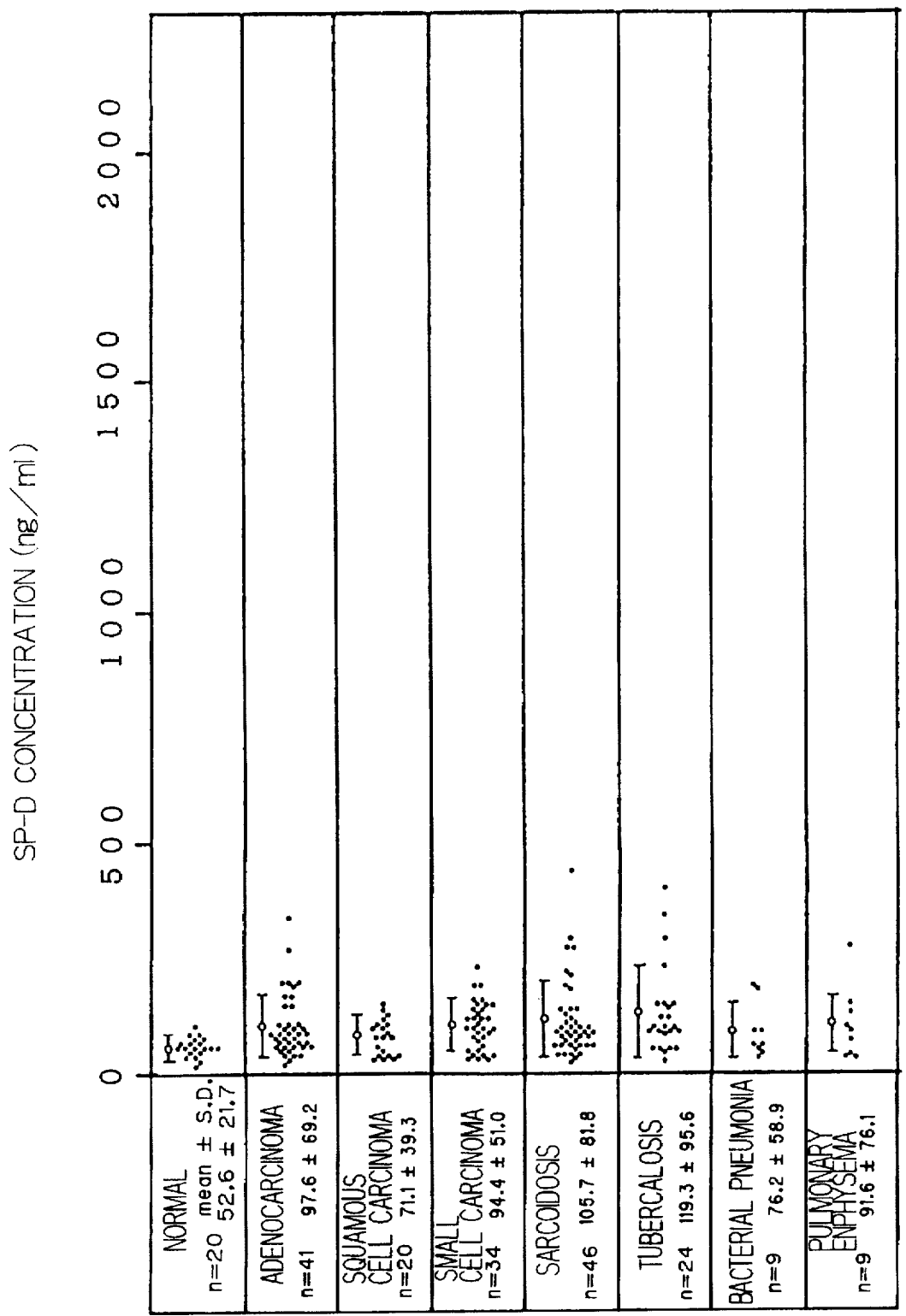
FIG. 10 shows the results of SP-D levels determined by the sandwich ELISA in sera from patients with various respiratory diseases including squamous cell carcinoma, adenocarcinoma, sarcoidosis, tuberculosis, pulmonary emphysema, bacterial pneumonia and small cell carcinoma, and from healthy volunteers.
Figure 11:
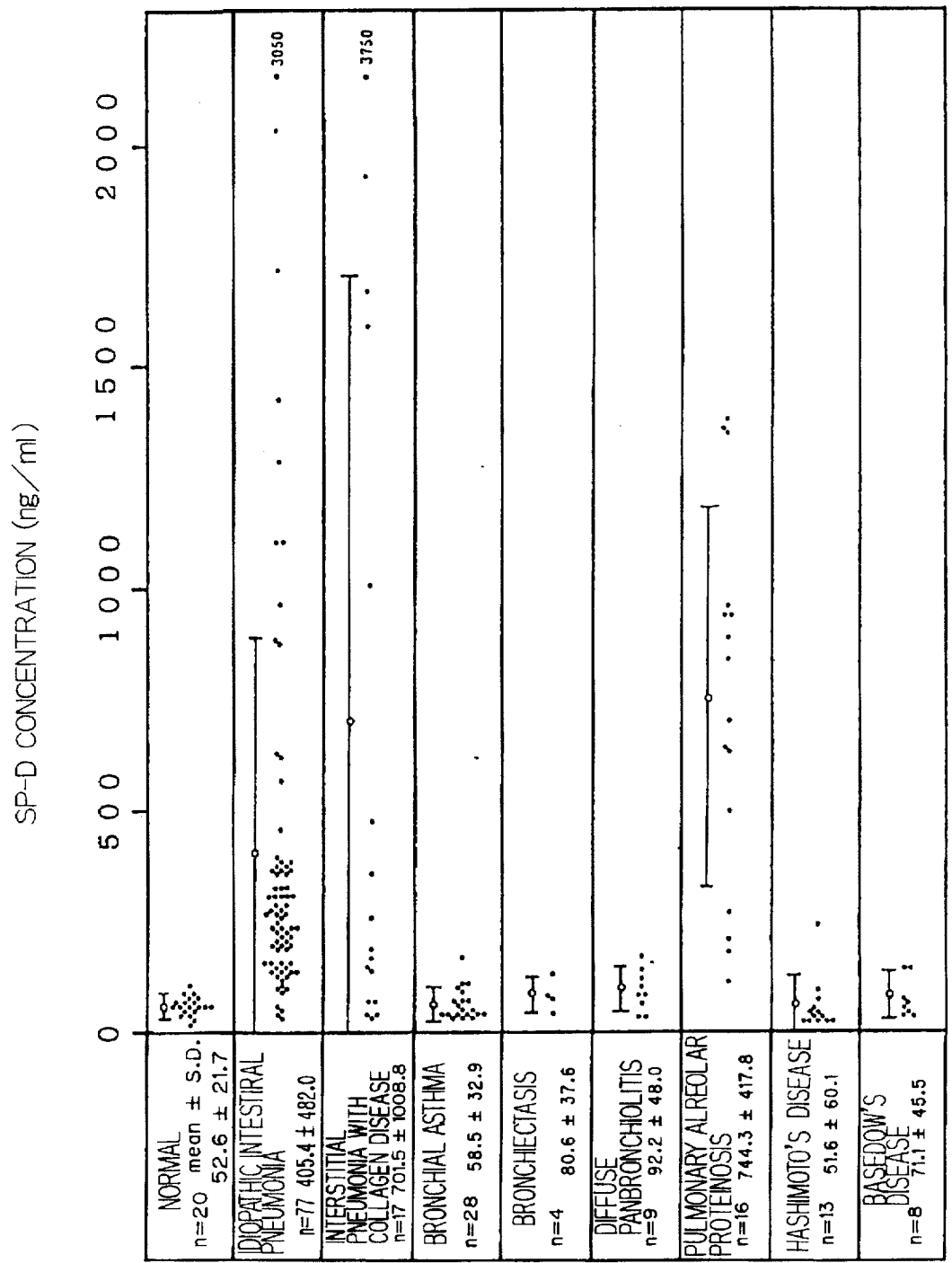
FIG. 11 shows the results of SP-D levels determined by the sandwich ELISA in sera from patients with various respiratory diseases including idiopathic interstitial pneumonia, interstitial pneumonia with collagen disease, pulmonary alveolar proteinosis, bronchial asthma, bronchiectasis, diffuse panbronchiolitis, Hashimoto's disease and Basedow's disease, and from healthy volunteers.

(C) SP-D levels in sera obtained from patients with various respiratory diseases The SP-D levels were assayed in sera obtained from patients with various respiratory diseases such as idiopathic interstitial pneumonia, interstitial pneumonia with collagen disease, pulmonary alveolar proteinosis, squamous cell carcinoma, adenocarcinoma, small cell carcinoma, sarcoidosis, tuberculosis, pulmonary emphysema, bacterial pneumonia, bronchial asthma, bronchiectasis and diffuse panbronchiolitis, and for control, sera from healthy volunteers. As the result, the SP-D levels were obviously higher in the patients with interstitial pneumonia such as idiopathic interstitial pneumonia and interstitial pneumonia with collagen disease, and with pulmonary alveolar proteinosis, as compared to that of healthy volunteers, as shown in FIGS. 10 and 11. It is thus demonstrated that it would be effective for judgment and diagnosis of the various diseases described above to determine the SP-D levels in sera.

EXAMPLE 6

Immunologically Staining of Tissues

Lung cancer tissues (i.e., adenocarcinoma, squamous cell carcinoma, large cell carcinoma, small cell carcinoma) obtained by surgical operation and autopsy and cancer tissues of other organs were fixed with formalin and embedded in paraffin. Then immunohistological examination was performed according to ABC method.

That is, after sufficiently removing the paraffin with xylene, tissue slices were hydrated by changing an ethanol concentration stepwise and then washed with water. Next, the slices were immersed at room temperature for 30 minutes in methanol containing 0.3% hydrogen peroxide thereby to remove the endogenous peroxidase activity, and then in PBS for 5 minutes for rinsing. This lavage procedure was repeated three (3) times. Next, the slices were immersed in 10% horse serum-containing PBS at room temperature for 30 minutes to perform blocking. Thereafter, the monoclonal anti-human SP-D antibody or monoclonal anti-human SP-A antibody appropriately diluted with PBS was dropped onto the slices to react them at room temperature for 30 minutes. The slices were then washed with PBS in a similar manner. Next, biotinylated anti-mouse IgG antibody (manufactured by Vector Laboratories Inc.) was dropped on the slices to react at room temperature for 30 minutes. The slices were then washed with PBS likewise. Subsequently, ABC Reagent (manufactured by Vector Laboratories Inc.) was dropped onto the slices to cause reaction at room temperature for 30 minutes. After washing three (3) times with PBS, peroxidase substrate solution (manufactured by Vector Laboratories Inc.) was dropped on the slices to cause reaction at room temperature. At the time when a color was appropriately formed, the slices were washed to terminate the color-forming reaction. The slices were then sealed.

As the result, SP-D was positive in 25 out of 36 cases with adenocarcinoma and 4 out of 5 cases with squamous cell carcinoma, respectively, whereas SP-D was negative in all other cases of tissue type lung cancer and cancers of other organs. With regard to SP-A levels tested simply for reference, SP-A was positive in 18 out of 36 cases with adenocarcinoma and, at least one of SP-D and SP-A was positive in 31 out of 36 cases. From the foregoing results it was confirmed that use of the antibodies to SP-D and SP-A in combination improved a positive rate and was thus more useful for diagnosis of lung-primary adenocarcinoma. Typical examples of the immunologically stained lung tissue of adenocarcinoma and squamous cell carcinoma using the monoclonal anti-human SP-D antibody 6B2 are shown in FIGS. 12 and 13.

Industrial Applicability

The monoclonal antibody of the present invention is capable of specifically binding with human pulmonary surfactant apoprotein D. By using such a monoclonal antibody as an antibody reagent, human pulmonary surfactant apoprotein D can be specifically detected or determined for the first time. The monoclonal antibody of the present invention is therefore useful as a tool for clarifying the function of human pulmonary surfactant apoprotein D. In addition, the method for detection or determination of human pulmonary surfactant apoprotein D and the kit for use in the method are useful for diagnosis of respiratory diseases such as IRDS, ARDS, pulmonary alveolar proteinosis, interstitial pneumonia, adenocarcinoma and squamous cell carcinoma.

We claim:

1. A method for screening interstitial pneumonia in a patient suspected of suffering from respiratory disease, which comprises the steps of:

contacting a liquid sample obtained from the patient with a monoclonal antibody or fragment thereof which specifically binds to human pulmonary surfactant apoprotein D;

measuring the presence of an immune complex formed between the antibody or fragment thereof and human pulmonary surfactant apoprotein D in the liquid sample; and comparing the amount of measured immune complex with a standard value of immune complex for a normal individual so as to assess the presence or absence of interstitial pneumonia in the patient;

wherein the monoclonal antibody or fragment has the following additional characteristics:

(1) specificity: the monoclonal antibody or fragment does not substantially react with other human antigenic substances but specifically reacts only with human pulmonary surfactant apoprotein D;

(2) reactivity: the monoclonal antibody or fragment reacts with human pulmonary surfactant apoprotein D in a concentration-dependent manner;

(3) cross-reactivity: the monoclonal antibody or fragment does not substantially react with human pulmonary surfactant apoproteins A, B and C; and (4) species specificity: the monoclonal antibody or fragment does not substantially react with rat pulmonary surfactant apoprotein D.

2. The method according to claim 1, wherein the sample is serum.

3. The method according to claim 1, wherein the interstitial pneumonia is idiopathic interstitial pneumonia.

4. The method according to claim 1, wherein the interstitial pneumonia is interstitial pneumonia with collagen disease.

5. A method for screening adenocarcinoma in a patient suspected of suffering from respiratory disease, which comprises the steps of:

obtaining a lung tissue sample from the patient to prepare a lung tissue specimen;

contacting the thus prepared lung tissue specimen with a monoclonal antibody or fragment thereof which specifically binds to human pulmonary surfactant apoprotein D;

detecting the presence or absence of human pulmonary surfactant apoprotein D in the sample by detecting the presence or absence of an immune complex formed between the antibody or fragment and human pulmonary surfactant apoprotein D in the specimen; and comparing the presence of absence of immune complex in the lung tissue specimen with a control tissue specimen so as to assess the presence or absence of adenocarcinoma in the patient, wherein the monoclonal antibody or fragment has the following additional characteristics:

(1) specificity: the monoclonal antibody or fragment does not substantially react with other human antigenic substances but specifically reacts only with human pulmonary surfactant apoprotein D;

(2) reactivity: the monoclonal antibody or fragment reacts with human pulmonary surfactant apoprotein D in a concentration-dependent manner;

(3) cross-reactivity: the monoclonal antibody or fragment does not substantially react with human pulmonary surfactant apoproteins A, B and C; and (4) species specificity: the monoclonal antibody or fragment does not substantially react with rat pulmonary surfactant apoprotein D.

6. A method for screening squamous cell carcinoma in a patient suspected of suffering from respiratory disease, which comprises the steps of:

obtaining a lung tissue sample from the patient to prepare a lung tissue specimen;

contacting the thus prepared lung tissue specimen with a monoclonal antibody or fragment thereof which specifically binds to human pulmonary surfactant apoprotein D;

detecting the presence or absence of human pulmonary surfactant apoprotein D in the sample by detecting the presence or absence of an immune complex formed between the antibody or fragment and human pulmonary surfactant apoprotein D in the specimen; and comparing the presence or absence of immune complex in the lung tissue specimen with a control tissue specimen so as to assess the presence or absence of squamous cell carcinoma in the patient, wherein the monoclonal antibody or fragment thereof has the following additional characteristics:

(1) specificity: the monoclonal antibody or fragment does not substantially react with other human antigenic substances but specifically reacts only with human pulmonary surfactant apoprotein D;

(2) reactivity: the monoclonal antibody or fragment reacts with human pulmonary surfactant apoprotein D in a concentration-dependent manner;

(3) cross-reactivity: the monoclonal antibody or fragment does not substantially react with human pulmonary surfactant apoproteins A, B and C; and (4) species specificity: the monoclonal antibody or fragment does not substantially react with rat pulmonary surfactant apoprotein D.

\* \* \* \* \*